United States Patent [19]

Toriyama et al.

[11] Patent Number: 5,178,901
[45] Date of Patent: Jan. 12, 1993

[54] TITANIUM METAL-COATING MATERIAL, METHOD FOR PRODUCTION THEREOF, METHOD FOR COATING THEREWITH, AND PRODUCT COATED THEREWITH

[75] Inventors: Motohiro Toriyama, Kasugai; Sukezo Kawamura, Inuyama; Yukari Kawamoto, Showa; Yoshiyuki Yokogawa, Meito; Takahiro Suzuki, Kita, all of Japan

[73] Assignees: Agency of Industrial Science & Technology; Ministry of International Trade & Industry, both of Tokyo, Japan

[21] Appl. No.: 618,750

[22] Filed: Nov. 27, 1990

[30] Foreign Application Priority Data

Dec. 2, 1989 [JP] Japan .................................. 1-313909

[51] Int. Cl.$^5$ .............................................. B05D 3/02
[52] U.S. Cl. ...................................... 427/2; 427/376.4
[58] Field of Search ................................. 427/2, 376.4

[56] References Cited

U.S. PATENT DOCUMENTS

| | | | |
|---|---|---|---|
| 4,145,764 | 3/1979 | Suzuki et al. | 427/2 |
| 4,146,936 | 4/1979 | Aoyagi et al. | 427/2 |
| 4,746,532 | 5/1988 | Suzuki et al. | 427/2 |
| 4,847,163 | 7/1989 | Shimamune et al. | 427/2 |
| 4,990,163 | 2/1991 | Ducheyne et al. | 427/2 |

*Primary Examiner*—Janyce Bell
*Attorney, Agent, or Firm*—Oblon, Spivak, McClelland, Maier & Neustadt

[57] ABSTRACT

A powder for coating the surface of a titanium metal is obtained by mixing compounds as raw materials for CaO, TiO$_2$, and P$_2$O$_5$ with a small amount of a Na$_2$O-containing compound, fusing the resultant mixture, and solidifying and pulverizing the fused mixture. A coating of a calcium phosphate compound adhering with great fastness to the surface of the titanium metal is formed by preparing an aqueous slurry containing the powder mentioned above, applying the aqueous slurry to the surface of the titanium metal, and heat-treating the coated titanium metal.

1 Claim, No Drawings

TITANIUM METAL-COATING MATERIAL, METHOD FOR PRODUCTION THEREOF, METHOD FOR COATING THEREWITH, AND PRODUCT COATED THEREWITH

BACKGROUND OF THE INVENTION

1. Field of the Invention

This invention relates to a material capable of forming a coating film adhering with great fastness to the surface of titanium or a titanium alloy (hereinafter referred to as "titanium metal"), a method for the production of the material, a method for coating a titanium metal with the material, and titanium metal article coated with the material. This material is compatible with living tissues.

2. Description of the Prior Art

Since titanium and titanium alloys possess high strength and exhibit no toxicity to living tissues, efforts are being continued to realize their utility as materials for artificial roots of teeth, artificial bones, and artificial joints. The materials using titanium as a main component, however, do not promote osteoinduction, osteoconduction or bonding of new bones because they are inactive relative to living tissues. These materials, therefore, are incapable of being kept buried in living tissues in a stable state for a long time. In contrast, the calcium phosphate compounds such as apatite hydroxide and tricalcium phosphate that are the main components of such living inorganic substances as bones and teeth, exhibit excellent bioaffinity for living tissues in terms of nontoxicity, osteoconduction property, bone bonding property, and bone replacement property. Sintered articles of calcium phosphate compounds, however, have low mechanical strength and, therefore, have limited utility. In view of the circumstances described above, a composite material comprising titanium or a titanium alloy as a substrate and a coating of calcium phosphate covering the surface of the substrate and having a property of bioaffinity and high strength is desired.

The conventional methods of coating a materials having titanium as its main component with a calcium phosphate compound are of three types, (1) the flame spraying method, (2) the spattering method, and (3) the dispersing method. The flame spraying method comprises dissolving calcium phosphate powder in a flame or a plasma kept at a high temperature and spraying the dissolved powder at a high speed on the surface of a material formed mainly of titanium. Since this method has to be conducted at high temperature, it often induces decomposition of the calcium phosphate and alteration of the crystalline structure of the compound. The spattering method comprises spattering a calcium phosphate compound onto the surface of a material having titanium as its main component. Since this method requires the spattering in a high degree of vacuum, the productivity is low and the cost of production is high. Moreover, it is difficult to produce a coating layer of a sufficient thickness by this method. The glass dispersing method comprises dispersing a calcium phosphate compound in molten glass, applying the resultant molten glass on the surface of a material comprising titanium as its main component, and solidifying the applied coating by cooling. The coating material prepared by this method is deficient in durability in living tissue because the dissolving speed of glass type material is higher than that of a crystal type material in living tissues.

As described above, each of the conventional methods for coating a surface with calcium phosphate has its defects.

In the circumstances, it is a need to develop a commercially feasible method of coating a titanium metal with calcium phosphate, inexpensively with a simple device.

SUMMARY OF THE INVENTION

The present inventors continued a study with a view to meeting this need and found that a $CaO\text{-}TiO_2\text{-}P_2O_5$ type glass excels in fast adhesiveness to a material having titanium as its main material and, when heat-treated under suitable conditions, crystallizes into calcium phosphate and calcium titano-phosphate. The present invention has been completed on the basis of this knowledge.

To be specific, this invention is directed to a method for the production of a powdery material for coating the surface of a titanium metal, comprising mixing compounds as raw materials for $CaO$, $TiO_2$, and $P_2O_5$ in amounts to give a molar ratio of $CaO:TiO_2:P_2O_5$, in the range of 9:4.6~5.4:5.6~6.4, adding to the resultant mixture a sodium compound in an amount to give a concentration as $Na_2O$ in the range of 1 to 5 mol % based on the amount of said mixture, fusing by heating the resultant mixture at a temperature of at least 1,200° C., cooling the resulting vitrified melt, and pulverizing the resultant solid to a powdery material for coating the surface of a titanium metal produced by the method described above, to a method for forming a coating of a calcium phosphate compound on the surface of a titanium metal, comprising converting the aforementioned powdery material into an aqueous slurry, applying the aqueous slurry on the surface of the titanium metal, and heating the titanium metal coated with the aqueous slurry to a temperature in the range of 600° to 1,300° C., and a titanium metal material coated with the calcium phosphate compound obtained by the method described above.

DETAILED DESCRIPTION OF THE PREFERRED EMBODIMENTS

In the present invention, the optimum value of the molar ratio of $CaO:TiO_2:P_2O_5$ is 9:5:6.

It is necessary that the molar ratio of $CaO:TiO_2:P_2O_5$ should fall in the range of 9:4.6~5.4:5.6~6.4.

As regards the raw materials for $CaO$, $TiO_2$, and $P_2O_5$, calcium carbonate may be used for $CaO$ and phosphoric acid for $P_2O_5$, for example.

In this invention, the compounds as raw materials containing $CaO$, $TiO_2$, and $P_2O_5$ are mixed with a sodium compound containing $Na_2O$ and the resultant mixture is fused by heating. The heating temperature used in this case has to be sufficient to dissolve the raw materials and is at least 1,200° C. The raw material powder for coating the surface of a titanium metal can be obtained by cooling the fused raw materials and pulverizing the resultant solid.

Now, the method for coating the surface of a titanium metal with a calcium phosphate compound by the use of the raw material mentioned above will be described.

First, an aqueous slurry of the aforementioned raw material powders is prepared. This aqueous slurry may be produced by mixing the raw material powders produced by the method described above with water. Otherwise, it may be obtained by casting the fused mixture into water thereby preparing amorphous glass and pulverizing the glass in conjunction with water added thereto. The aqueous slurry is required to have a powder concentration sufficient to enable the aqueous slurry to be applied effectively to the surface of a titanium metal. This concentration is desired to be in the range of 15 to 25% by weight.

The aqueous slurry is applied to the surface of a titanium metal. The method used for this application is not critical. It can be easily carried out by any of the known methods such as, for example, the spraying method or the dipping method.

Then, by heat-treating the surface of the titanium metal coated with the aqueous slurry at a temperature in the range of 650° to 1,300° C., calcium phosphate can be attached with high fastness to the surface.

As a result, a material of titanium metal coated with calcium phosphate can be obtained.

The process of fusion and crystallization of glass during the heat treatment of the surface of a titanium metal coated with the aqueous slurry in the method of the present invention will be described more specifically. During the initial phase of the heat treatment, the glass powder for the coating material is softened by fusion, caused to adhere fast to the surface of the material using titanium as a main component and, at the same time, enabled to react with the titanium oxide phase present in the surface region of the titanium material and gain in adhesive strength. In the latter phase of the heat treatment, the formation of crystal seeds of calcium phosphate and calcium titano-phosphate and the growth of crystals proceed and the crystallization of calcium phosphate and calcium titanophosphate is completed. No amorphous phase remains. The coating layer, therefore, has high durability in living tissues.

The $Na_2O_2$ which is incorporated in the raw material powder in a concentration in the range of 1 to 5 mol % serves the purpose of accelerating the crystallization of calcium phosphate and calcium titanophosphate in the latter phase of the aforementioned heat treatment.

The method of this invention is capable of coating the surface of a titanium metal with calcium phosphate, inexpensively by the use of a simple device. Thus, this method has very high industrial utility.

The calcium phosphate material for coating the surface of titanium metal which is obtained by the method of this invention has a excellent bioaffinity and high strength, and can be used advantageously in such medical materials as artificial bones, artificial joints, and artificial tooth roots.

Now, the present invention will be described more specifically with reference to working examples.

EXAMPLE 1

A raw material was prepared by mixing calcium carbonate, titanium dioxide (anatase), and phosphoric acid in amounts to give a molar ratio, $CaO:TiO_2:P_2O_5$, of 9:5:6. This raw material and 2 mol % of sodium carbonate added thereto were fused at 1,850° C. The formed metal was cast into water to produce amorphous glass. A slurry containing 20% of the glass was prepared by pulverizing the amorphous glass in conjunction with added water. This slurry was applied by the spraying method to a titanium material. The coated material was dried and then heat-treated at 690° C. for 23 hours.

Consequently, the surface of this titanium material was coated with a calcium phosphate layer 200 μm in thickness. The calcium phosphate adhered fast to the titanium material.

EXAMPLE 2

The procedure of Example 1 was faithfully repeated, except that the temperature of the heat treatment was changed to 800° C. and the time of this heat treatment was reduced to one hour.

Consequently, there was obtained a titanium material whose surface was coated with a calcium phosphate layer 100 μm in thickness.

EXAMPLE 3

The procedure of Example 1 was faithfully repeated, except that the temperature of the heat treatment was changed to 1,200° C., the time of the heat treatment was reduced to one hour, and the heat treatment was carried out in a vacuum furnace.

Consequently, there was obtained a titanium material whose surface was coated with a calcium phosphate layer 100 μm in thickness.

COMPARATIVE EXPERIMENT 1

The procedure of Example 1 was faithfully repeated, except that the treatment for converting the raw material powder for coating into amorphous glass was omitted.

Consequently, no fast adhering coating layer was formed on the surface of the titanium material.

COMPARATIVE EXPERIMENT 2

The procedure of Example 1 was faithfully repeated, except that the fusing temperature of the raw material was changed to 900° C.

Consequently, the surface of the titanium material underwent oxidation and no coating layer was formed on the surface.

What is claimed is:

1. A method for the formation of a coating of a calcium phosphate on the surface of a titanium metal, which comprises:

mixing CaO, $TiO_2$ and $P_2O_5$ in amounts to give a molar ratio in the range of 9:4.6 to 5.4:5.6 to 6.4 to obtain a first mixture;

adding to said first mixture a sodium compound in an amount to give a molar concentration, calculated in terms of $Na_2O$, in the range of 1 to 5 mol % of said first mixture, thereby obtaining a second mixture;

fusing said second mixture by heating to a temperature of at least 1,200° C. to produce a vitrified melt;

preparing an aqueous slurry containing said vitrified melt;

applying said aqueous slurry on the surface of a titanium metal; and heat-treating said titanium metal coated with said aqueous slurry at a temperature in the range of 600° to 1,300° C.

* * * * *